United States Patent [19]

Faure et al.

[11] Patent Number: 6,054,557
[45] Date of Patent: Apr. 25, 2000

[54] FLUORESCENT PEPTIDES

[75] Inventors: Marie-Pierre Faure, Quebec, Canada; Jean-Pierre Vincent, Cagnes sur Mer; Georges Gaudriault, Nice Cedex, both of France; Alain Beaudet; Clarissa Desjardins, both of Quebec, Canada

[73] Assignee: Advanced Bioconcept (1994) Ltd., Montreal, Canada

[21] Appl. No.: 08/682,810

[22] Filed: Jul. 10, 1996

Related U.S. Application Data

[63] Continuation-in-part of application No. 08/504,856, Jul. 20, 1995, abandoned, which is a continuation-in-part of application No. 08/475,751, Jun. 7, 1995, Pat. No. 5,824,772, which is a continuation-in-part of application No. 08/416,007, Apr. 4, 1995, Pat. No. 5,693,679.

[51] Int. Cl.$^7$ ..................................................... C07K 7/00
[52] U.S. Cl. .......................... 530/350; 530/302; 530/324; 435/7.1
[58] Field of Search .................................. 530/350, 302, 530/324; 435/7.1

[56] References Cited

U.S. PATENT DOCUMENTS 4,046,633  9/1977  Keutel .............................. 195/103.5 R

FOREIGN PATENT DOCUMENTS

| | | |
|---|---|---|
| 0 240 914 A2 | 10/1987 | European Pat. Off. |
| 0 333 071 | 11/1988 | European Pat. Off. |
| 0 331 126 A2 | 9/1989 | European Pat. Off. |
| 0 466 565 A1 | 1/1992 | European Pat. Off. |
| 0 606 804 | 7/1994 | European Pat. Off. |
| 0 608 987 | 8/1994 | European Pat. Off. |
| 27 02 699 A1 | 12/1977 | Germany. |
| 63-051400 | 3/1988 | Japan. |
| 2 291 708 | 1/1996 | United Kingdom. |
| WO 93/04194 | 3/1993 | WIPO. |
| WO 93/18068 | 9/1993 | WIPO. |
| WO 95/22341 | 8/1995 | WIPO. |
| WO 96/31531 | 10/1996 | WIPO. |
| WO 97/04311 | 2/1997 | WIPO. |

OTHER PUBLICATIONS

Amoscato et al., Peptide Protein Res., 29:177–186, 1987.
Ashworth et al., Proc Natl Acad Sci USA, 92:512–516, 1995.
Bowden et al., Proc Natl Acad Sci USA, 91:8964–8968, 1994.
Cardullo et al., Developmental Biology, 162:600–607, 1994.
Carraway et al., J of Biol Chem, 248:6854–6861, 1973.
Cauvin et al., Regulatory Peptides, 35:161–1173, 1991.
Chard, Laboratory Techniques in Biochemistry and Molecular Biology, Elzevier Biomedical Press, New York.
Cheng et al., FEBS Letters, 100: 113–116, 1979.
Christophe, Biochimica et Biophysica Acta, 1154:183–199, 1993.

(List continued on next page.)

*Primary Examiner*—Cecilia J. Tsang
*Assistant Examiner*—C. Delacroix Muirheid
*Attorney, Agent, or Firm*—Clark & Elbing LLP

[57] ABSTRACT

The invention provides biologically active compounds of the formula:

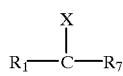

where $R_1$ is a light-emitting moiety and $R_7$ is a peptide of between 2 and 200 amino acids. X is selected from the group including $=O$, $=S$, $-OH$, $=C=O$, $=NH$, $-H$, $-OR$, $-NR$, $-R$, $-R_3R_4$, wherein each R, $R_4$ and $R_3$, independently, is H or a C1–C6 branched or unbranched, substituted or unsubstituted, alkyl. The compounds are both biologically active and optically detectable. The peptide is chemically attached to the light-emitting moiety at an amino acid position which is not involved in binding to the peptide's receptor. In this way, the peptide's affinity for its receptor is not significantly decreased, and the compound retains high biological activity and can be easily detected using standard optical means.

35 Claims, 5 Drawing Sheets

OTHER PUBLICATIONS

Cushman, Biochemical Pharmacology, 20:1637–1648, 1971.
Epelbaum, Basic and Chemical Aspects of Neuroscience, 4:17–28, 1992.
Faure et al., Annals of the New York Academy of Sciences, 668:345–347, 1992.
Faure et al., The Journal of Histochemistry and Cytochemistry, 42:755–763, 1994.
Guillon et al., Peptides, 13:7–11, 1992.
Haigler et al., Proc Natl Acad Sci USA, 75:3317–3321, 1978.
Haugland et al., Noninvasive Techniques in Cell Biology:1–20, Wiley–Liss, Inc., 1990.
Hazum et al., Proc Natl Acad Sci USA, 77:3038–3041, 1979.
Hazum et al., Biochemical & Biophysical Research Communications, 88:841–846, 1979.
Kitabgi et al. (eds), Annals NY Acad Sci, 668:Table of Contents.
Kohzuki et al., Neuroscience, 42:245–260, 1991.
Melander et al., Handbook of Chemical Neuropanatomy, vol. II, Elsevier Publishers, 1992.
Merchenthaler et al., Prog Neurobiol, 40:711–769, 1993.
Nawa et al., Nature, 306:32–36, 1983.
Roettger et al., Journal of Cell Biology, 130:579–590, 1995.
Rubanyi et al., Pharmacological Reviews, 46:325–415, 1994.
Sack et al., Cell Tissue Research, 228:183–204, 1983.
Sadoul et al., Biochem and Biophys Res Comm 120:206–213, 1984.
Shecter et al., Proc. Natl. Acad. Sci. USA, 75:2135–2139, 1978.
Sigma Immuno Chemicals Company, FlouroTag FITC Conjucation Kit, 1994.
Song et al., Journal of Comparative Neurology, 316:467–484, 1992.
St. John et al., Journal of Neuroscience, 6:1492–1512, 1986.
Tanaka et al., Neuron, 4:947–854, 1990.
Tota et al., Journal of Biological Chemistry, 270:26466–26472, 1975.
Tota et al., Biochemistry, 33:13079–13086, 1994.
Vrontakis et al., Journal of Biological Chemistry, 262:16755–16758, 1987.
Walker et al., Molecular and Cellular Endocrinology, 91:107–112, 1993.
Yamada et al., Proc. Nat. Acad. Sci., 89:251–255, 1992.
Yanagisawa et al., Nature, 332:411–415, 1988.
Zhuo et al., Kidney International, 44:S40–S46, 1993.
Zhao, Journal of Chromatography, 608:239–242, 1992.
International search report for PCT/CA97/00481 mailed Nov. 13, 1997.
Steinkamp, John A., "Flow cytometry," Rev. Sci. Instrum. 55(9):1375–1400, 1984.
Goldstein et al., *Proc. Natl. Acad. Sci U.S.A.*, 85(19), pp. 7375–7379, 1988.

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Cys Ser Cys Ser Ser Leu Met Asp Lys Glu Cys Val Tyr Phe Cys His
 1               5                  10                  15

Leu Asp Ile Ile Trp
            20

<210> SEQ ID NO 2
<211> LENGTH: 29
<212> TYPE: PRT
<213> ORGANISM: Homo sapiens

<400> SEQUENCE: 2

Thr Leu Gly His Lys Asp Ser Phe Ser Arg His Asn Asp Ile Ala His
 1               5                  10                  15

Pro Gly Leu Leu Tyr Gly Ala Ser Asn Leu Thr Trp Gly
            20                  25
```

FLUORESCENT PEPTIDES

BACKGROUND

This application is a continuation-in-part of U.S. Ser. No. 08/504,856, filed Jul. 20, 1995 and entitled "Fluorescent Peptides", now abandoned, which is a continuation-in-part of U.S. Ser. No. 08/475,751, filed Jun. 7, 1995 and entitled "Fluorescent Somatostatin", now U.S. Pat. No. 5,824,772, which is a continuation-in-part of U.S. Ser. No. 08/416,007, having the same name and filed Apr. 4, 1995, now U.S. Pat. No. 5,693,679.

This invention relates to peptide-based compounds having light-emitting moieties.

Detectably labelled peptides provide useful reagents for monitoring peptide, cytokine, drug, and hormone receptors at the cellular level. Typically, the labelled peptide is placed in contact with a tissue or cell culture where it binds an available receptor. Once bound, the label is detected, allowing properties such as receptor distribution or receptor binding kinetics to be monitored.

SUMMARY OF THE INVENTION

The invention provides a compound containing a peptide and a light-emitting moiety which is both biologically active and optically detectable. The peptide is chemically attached to the light-emitting moiety at an amino acid position which is not involved in binding to the peptide's receptor. In this way, the peptide's affinity for its receptor is not significantly decreased, and the compound retains high biological activity and can be easily detected using standard optical means.

In general, in one aspect, the invention provides a biologically active compound of the formula:

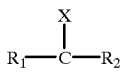

where $R_1$ is a light-emitting moiety; $R_2$ is a peptide of between 2 and 200 amino acids which is not neurotensin; and X is selected from the group consisting of =O, =S, —OH, =C=O, =NH, —H, —OR, —NR, —R, —$R_3R_4$, wherein each R, $R_4$, and $R_3$, independently, is H or a C1–C6 branched or unbranched, substituted or unsubstituted, alkyl. In another aspect, the invention provides a biologically active compound of the formula:

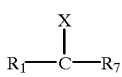

where $R_1$ is a light-emitting moiety and $R_7$ is a peptide of between 2 and 200 amino acids bound to C by a binding moiety selected from the group including the residues Ala, Arg, Asn, Asp, Cys, Gln, Gly, His, Ile, Leu, Lys, Met, Phe, Pro, Ser, Thr, Trp, Tyr, and Val. Preferably, in this case, the peptide $R_7$ is not neurotensin. In both cases, X is selected from the group including =O, =S, —OH, =C=O, =NH, —H, —OR, —NR, —R, —$R_3R_4$, wherein each R, $R_4$ and $R_3$, independently, is H or a C1–C6 branched or unbranched, substituted or unsubstituted, alkyl.

In yet another aspect, the invention provides a biologically active compound of the formula:

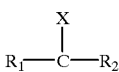

where $R_1$ is a light-emitting moiety, $R_2$ is a peptide of between 2 and 200 amino acids, and X is selected from the group consisting of =O, —OH, =C=O, =NH, —H, —OR, —NR, —R, —$R_3R_4$, where each R, $R_4$ and $R_3$, independently, is H or a C1–C6 branched or unbranched, substituted or unsubstituted, alkyl. Preferably, in this case, the peptide $R_2$ is not neurotensin.

In other aspects, a C1–C6 branched or unbranched, substituted or unsubstituted, alkyl serving as a "linker group" is disposed between the $R_2$ and C—X moieties. In this case, $R_2$ is preferably an opioid peptide and $R_7$ is preferably —NH (CH$_2$)$_5$NH—. In still other aspects, $R_2$ is neurotensin or an analogue thereof.

In preferred embodiments, both $R_2$ and $R_7$ are selected from the group including adrenocorticotrophic hormone, amylin, an amyloid beta-fragment, an atrial natriuretic peptide, bombesin, bradykinin, cadherin, calcitonin, a calcitonin-gene-related peptide, a casomorphin, a morphiceptin, cholecystokinin, corticotropin-releasing factor, deltorphin, a dermorphin, dynorphin, an endorphin, endothelin, enkephalin, fibronectin, galanin, a gonadotropin-associated peptide, a gonadotropin-releasing peptide, a growth factor or growth factor-related peptide, gastrin, glucagon, growth hormone-releasing factor, somatostatin, a GTP-binding protein fragment, inhibin, insulin, interleukin, lutenizing hormone-releasing hormone, magainin, melanocyte-stimulating hormone, a morphiceptin, a neurokinin, a neuromedin, neuropeptide-Y, an opioid peptide, oxytocin, a pancreatic polypeptide, a parathyroid hormone, a vasoactive intestinal polypeptide, Peptide YY, substance P, thyroid-releasing hormone, a toxin, vasopressin, and fragments, derivatives, and analogs thereof. Other possibilities for $R_2$ or $R_7$ are described in detail below. Most preferably, $R_2$ or $R_7$ are selected from the group consisting of endothelin and galanin.

In preferred embodiments, C is bonded to $R_2$ through an amino residue of an alpha carbon atom. Most preferably, $R_1$ is bound, through C, to a region of the $R_2$ peptide which is not involved in the peptide's biological activity, and the $R_2$ peptide binds to a human receptor.

In particular examples, $R_2$ is endothelin, and $R_1$ is bonded, through C, to the ninth amino acid residue of $R_2$ (e.g., the ε-amine group of Lys). If $R_2$ is galanin then $R_1$ is bonded, through C, to the fifth amino acid residue of $R_2$ (e.g., the ε-amine group of Lys).

In other preferred embodiments, $R_1$, the light-emitting moiety, is selected from the group including fluorescein, FTC, Texas Red, phycoerythrin, rhodamine, carboxytetramethylrhodamine, DAPI, indopyra dyes, Cascade blue coumarin, NBD, Lucifer Yellow, propidium iodide, a porphyrin, BODIPY, CY$^3$, CY$^5$, CY$^9$, and derivatives and analogs thereof. $R_1$ can be attached to C—X through a linking moiety selected from the group including indoacetamide, maleimide, isothyocyanate, succinimidyl ester, sulfonyl halide, aldehyde, glyoxal, hydrazine, and derivatives thereof.

In yet another aspect, the invention provides a method for generating a biologically active compound described above. The method includes the steps of reacting $R_1$ and $R_2$ in an aqueous solution to form a compound mixture; contacting the compound mixture with a receptor for $R_2$; and isolating from the compound mixture a compound exhibiting biological activity in the presence of the $R_2$ receptor.

Preferably, the isolating step includes the steps of binding the compound to the $R_2$ receptor; releasing the compound from the binding complex; and isolating the biologically active complex.

In another aspect, the invention provides a method for generating a biologically active compound of claim 1 which includes the steps of reacting $R_1$ and $R_2$ in an aqueous solution to form a compound mixture; contacting the compound mixture with a receptor for $R_2$; isolating from the compound mixture a compound exhibiting biological activity in the presence of the $R_2$ receptor; determining biologically inactive regions of the isolated compound; and synthesizing one of the above-described compounds by chemically attaching the light-emitting moiety to an amino acid comprised in the biologically inactive region. The final compound is then formed by attaching all other amino acids to form $R_2$.

In still other aspects of the invention, the above-described compounds are used for labelling cell receptor sites, cell sorting, flow cytometry, and performing fluorimmunoassays. For example, cell receptor sites can be imaged by contacting candidate cell receptor sites with one of the above-described compounds, and then detecting the bound compounds as an indication of the cell receptor sites. Cell sorting can be performed by contacting a population of candidate cells with an above-described compound, and isolating cells bound to the compound. Flow cytometry can be performed by contacting a population of cells with an above-described compound, and detecting cells bearing receptors on their surfaces by detecting cells bound to the compound.

In all cases, by "biologically active" is meant the compound binds to a receptor having an affinity ($IC_{50}$ value) for the compound which is at least 15 times that of the corresponding unlabelled peptide. More preferably, the $IC_{50}$ value for the compound is at least 10 times that of the corresponding unlabelled peptide. Most preferably, the $IC_{50}$ value for the compound is equal to or less than that of the corresponding unlabelled peptide. Receptor affinity, in this case, can be determined either using methods involving competition binding with radioactively labelled peptides or by using known methods of fluorescence polarization for measuring $K_d$ for the receptor-peptide interaction or other fluorescence techniques for measuring $K_d$.

By "peptide", as used herein, is meant a chain of amino acids of any length. Included in this term are proteins and polypeptides.

By "compound mixture", as used herein, is meant a mixture of peptides which are bound to light-emitting moieties at different amino acid positions. Such a mixture may contain peptides of varying lengths and varying biological activities.

The invention has many advantages. In a general sense, peptide-containing compounds which retain their biological activity after being labelled with light-emitting moieties have a wide variety of biological applications. Such compounds can be used effectively to identify, visualize, quantify, target, and select receptors on cells and tissues both in vitro and in vivo. These compounds obviate the use of more conventional labelled peptides, e.g., those attached to radioactive isotopes such as $^{125}I$. Radiolabelled compounds are often toxic, environmentally hazardous, chemically unstable, and have, by nature of the isotopes' radioactive decay rates, relatively short lifetimes. In contrast, the light-emitting biologically active compounds of the invention are relatively safe, non-toxic, easily disposable, and may be synthesized without employing any special laboratory procedures. In addition, because most light-emitting moieties are relatively stable, the compounds can be stored for extensive periods of time without undergoing significant degradation.

The compounds of the invention offer many additional advantages when employed in biological experiments. For example, peptides labelled with light-emitting moieties emit optical signals following excitation, and thus may be monitored by eye or with the aid of conventional, easy-to-use optical detectors (e.g., conventional charge-coupled devices (CCDs) or light-sensitive cameras). This method of detection is, in general, relatively simple and cost effective compared to detection of radioactive particles.

In addition, unlike radiolabelled, enzymatic, and colorimetric compounds, the compounds of the invention do not have to be incubated with secondary labelled compounds for detection. This means that the compounds can be used to monitor dynamic biological phenomena, such as the kinetics associated with receptor binding, in real time.

Furthermore, selection of biologically active compounds using a receptor binding assay is advantageous because it allows generation of useful biological labels in a rapid and efficient manner. In contrast, radiolabelled peptides typically require distinct and time-intensive steps for first isolating the labelled peptides and then determining their biological activity.

Other advantages and features of the invention will become apparent from the following detailed description, and from the claims.

DETAILED DESCRIPTION

Figure 1:
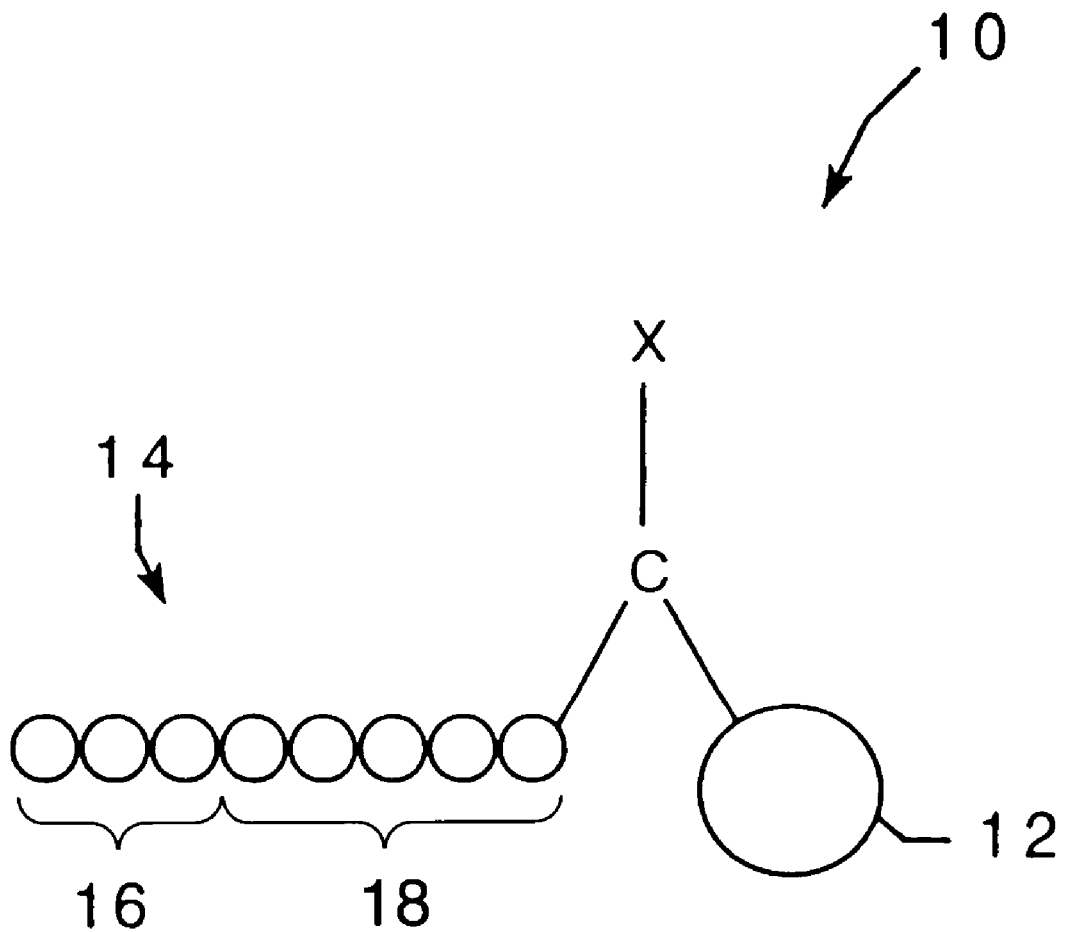
FIG. 1 is a schematic drawing of a compound containing a peptide and light-emitting moiety according to the invention.

As discussed above and shown in FIG. 1, biologically active and light-emitting, peptide-based compounds 10 according to the invention are generated by attaching a light-emitting moiety 12, such as a fluorescent dye, through a —(C—X)— bond to a peptide moiety 14. The peptide moiety contains both a biologically active region 16 and one or more "inactive" regions 18 (i.e, regions that are not significantly involved in the peptide's biological role). In one particular example, the biologically active region binds to the peptide's associated receptor, while the biologically inactive regions do not significantly participate in the peptide/receptor binding process. In general, to retain a biological activity for a fluorescent peptide that is comparable to that of the native peptide, the light-emitting moiety is chemically attached at a site within one of the peptide's biologically inactive regions. In this manner, the light-emitting moiety does not sterically hinder or otherwise significantly affect the region involved in, for example, receptor binding, and the biological activity of the compound is thus maintained at a high level.

In general, because of their relatively small size, the compounds of the invention preferably exhibit a 1:1 molar ratio between the light-emitting and peptide moieties. The attachment of more than one light-emitting moiety per peptide may, in some cases, result in a loss of biological activity. The 1:1 molar ratio is also important for the quantification of receptors during labelling applications, as it allows measured fluorescence intensity to be directly translated into a measure of binding peptide moieties which, in turn, allows the number of receptors to be determined. In addition, multiple fluorophores attached to a single peptide may result in fluorescence quenching, i.e., a loss of emission intensity which sometimes occurs when fluorophores are present in very close proximity to each other.

In addition to having amino acids available for receptor binding, the peptide compounds of the invention also contain light-emitting moieties which retain optical properties similar to those of the unbound fluorophore. In this way, the compound, even when bound to its receptor, emits light following absorption of an incident optical field, and thus serves as a marker for that particular receptor.

Figure 2:
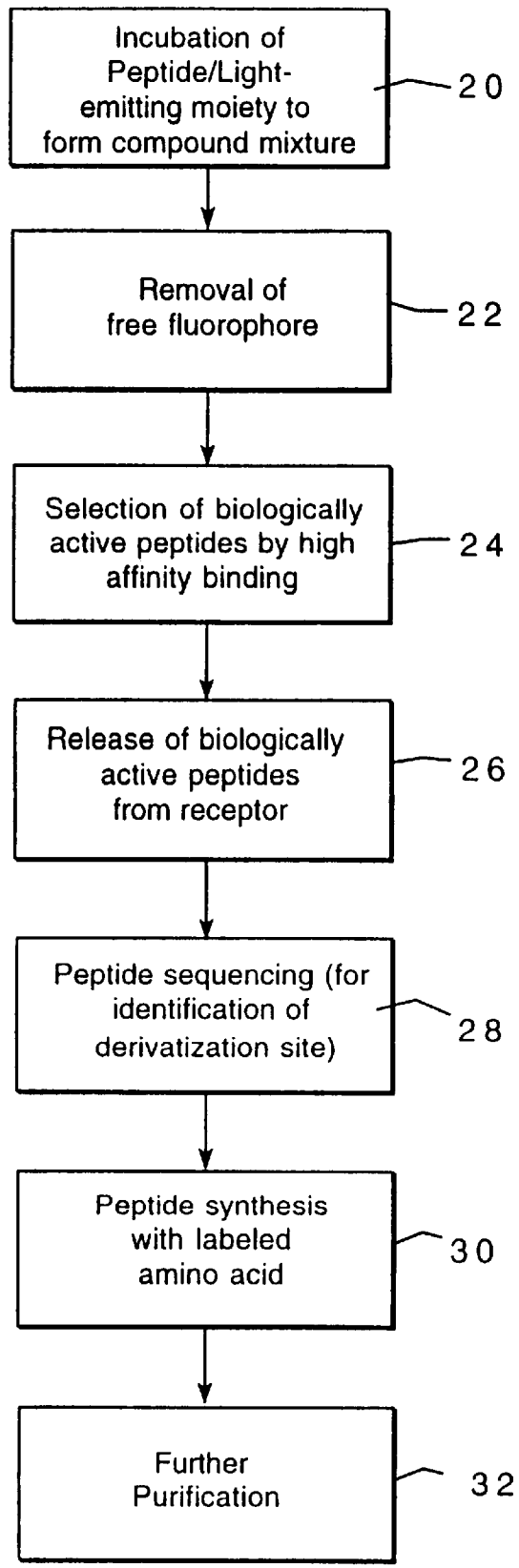
FIG. 2 is a flow chart showing the general synthetic procedure used to produce the compounds of the invention.

The general synthetic method for generating light-emitting biologically active compounds of the invention is shown in FIG. 2. This method begins with the step 20 of incubating the peptide and fluorophore of choice to form a mixture of compounds. Incubation is performed under conditions which permit optimal peptide labelling (see below). Typically, a solution containing the peptide of choice (preferably at a concentration of $10^{-2}$–$10^{-4}$M) is mixed with the light-emitting moiety in a highly basic solution (i.e., at a pH of 9.3–10.7), such as a carbonate buffer, in at least a 1:4 peptide:light emitting moiety molar ratio. The solution is mixed at room temperature for a time period of between about 24–48 hours, and is protected from light and shaken periodically. The resulting compound mixture includes biologically active and inactive whole peptides, cleaved fragments of peptides, and singly and multiply labelled peptides.

After covalent conjugation between the light-emitting moiety and peptide is allowed to occur, unbound fluorophore is removed (step 22). In general, this selection process can be performed using standard techniques, such a column chromatography or other analytical techniques known in the art. In a typical example, unreacted amounts of the free fluorophore are removed using a G-50 column equilibrated with phosphate-buffered saline (pH 7.4) and spun at 3000 rpm for a time period of between 5 and 20 minutes. The resultant eluent contains a mixture of labelled biologically active and inactive peptides.

This solution is then collected and subjected to a high-stringency pharmacological binding assay (step 24). In this assay, only biologically active compounds are bound to tissue receptors; inactive compounds are washed away. The assay is typically performed on tissue sections, receptor-coated columns, or membrane homogenates. In a typical example, an aliquot of the fluorescent peptide mixture is first dissolved in an aqueous solution (1:100) and incubated with an immobilized tissue sample containing high numbers of the peptide's receptor, e.g., receptor transfected membrane homogenates.

The selection process is designed to separate compounds exhibiting substantial biological activity from those relatively inactive compounds. If necessary, during the assay, binding of the biologically active compounds may be rapidly observed visually (from the sections or cells), in a fluorometer (from precipitated membrane homogenates), or by using more sensitive techniques such as fluorescence polarization spectroscopy.

The receptor-bound compounds are then removed from the tissue surface (step 26) and analyzed (step 28) to identify the site at which the fluorophore is attached (i.e., the site allowing fluorophore attachment without interference with receptor binding). Biologically active compounds bound to membrane receptors are separated from the remaining inactive fluorescent peptides in solution, either by centrifugation of membrane homogenates (typically at 3000 rpm for about 5 minutes at 4° C.) or, in the case of sections, by rapidly rinsing the sections in incubation buffer (3×1 minute) at 4° C. The membranes are then resuspended in binding buffer, with the biologically active compounds removed from the cell surface by incubation in a high salt/acid wash solution.

Once isolated, biologically active compounds are analyzed using known techniques, such as carboxypeptidase digestion and capillary electrophoresis, laser induced capillary zone electrophoresis, mass spectrometry, and/or HPLC or amino acid sequencing, to identify the site of attachment between the light-emitting moiety and the peptide.

Once the attachment site is determined, the appropriate amino acid can be attached directly to the light-emitting moiety prior to synthesis of the peptide. This allows the compound to be synthesized in a highly purified form using standard techniques, such as solid-phase peptide synthesis (step 30). If desired, the resulting complex can be further purified (step 32), preferably using a column-based method such as HPLC, and then eluted. In this manner, large quantities of biologically active, labelled peptide compounds can be easily generated in an automated fashion.

In general, reactions between peptides and light-emitting moieties are carried out by modifying amino acid functional groups, most typically a thiol or amine group, so that the moieties may be easily conjugated. Reactions for such modifications are described in the "Handbook of Fluorescent Probes and Research Chemicals—5th Edition" by Richard P. Haugland (1992), the contents of which are incorporated herein by reference. In general, thiols react with alkylating groups (R'—Z) to yield relatively stable thiol ethers (R—S—R'), with the leaving group Z preferably being a halogen (e.g., Cl, Br, or I) or a similar moiety. The most common reagents for derivatization of thiols are haloacetyl derivatives. Reaction of these reagents with thiols proceeds rapidly at or below room temperature in the physiological pH range.

Light-emitting moieties may also be attached to amino acid amine groups. The conditions used to modify amine moieties of the desired peptide will depend on the class of amine (e.g., aromatic or aliphatic) and its basicity. Aliphatic amines, such as the α-amino group of lysine, are moderately basic and reactive with acylating reagents. The concentration of the free-base form of aliphatic amines below pH 8 is very low; thus, the kinetics of acylation reactions of amines by isothiocyanates, succinimidyl esters, and other reagents is strongly pH-dependent. Although amine acylation reactions should usually be carried out above pH 8.5, the acylation reagents degrade in the presence of water, with the rate increasing as the pH increases. The α-amino function of the amino terminus usually has a $pK_a$ of ~7, thereby allowing it to be selectively modified by reaction at neutral pH.

In general, reactive groups on the light-emitting moiety, such as unsaturated alkyl groups, will react with the modified amino acid to form the compounds of the invention. The chemical structure of the light-emitting moiety may affect the synthetic route used to synthesize the compound. It may be necessary, for example, to modify the light-emitting moiety so that it includes a reactive group prior to exposure to the desired peptide.

The above technique has been used to synthesize a biologically active compound containing somatostatin and a light-emitting moiety which is described in U.S. Ser. No. 08/475,751 entitled "Fluorescent Somatostatin", filed Jun. 7, 1995, which is a continuation-in-part of U.S. Ser. No. 08/416,007, having the same name and filed Apr. 4, 1995, the contents of which are incorporated by reference.

Figure 3:
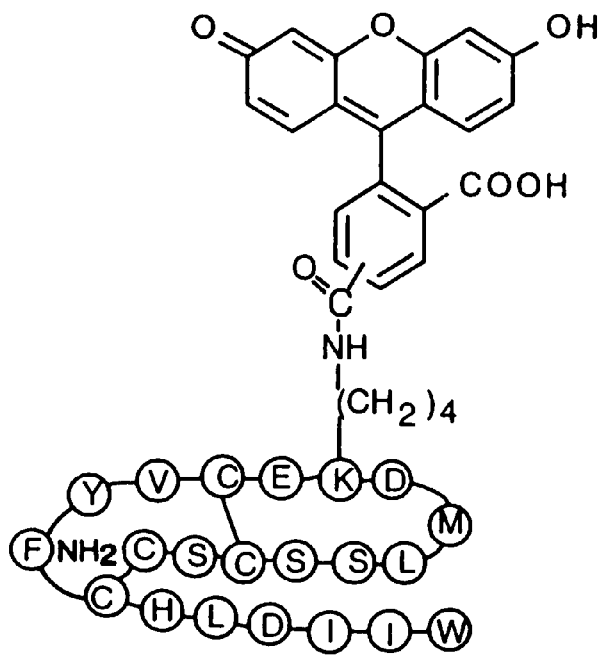
FIG. 3 is a schematic drawing of the chemical structure of fluorescent endothelin-1 (SEQ ID NO:1) according to the invention.
Figure 4:
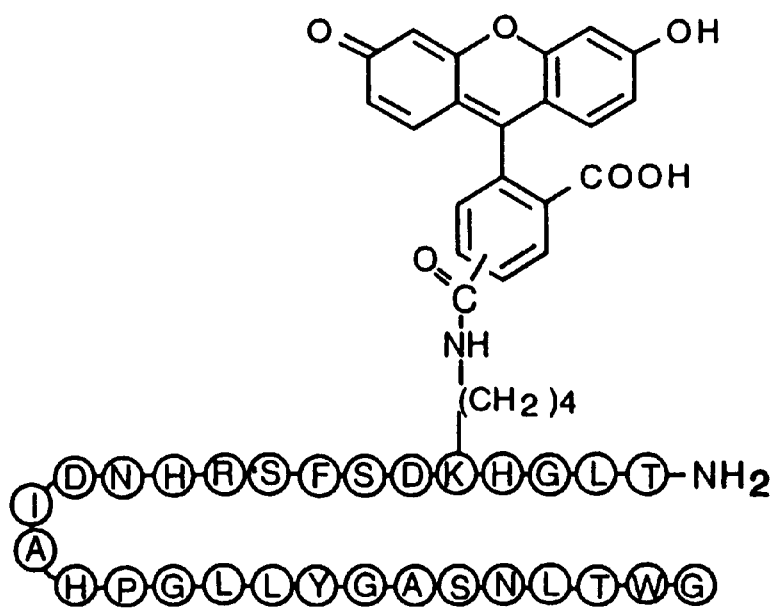
FIG. 4 is a schematic drawing of the chemical structure of fluorescent galanin (SEQ ID NO:2) according to the invention.

FIGS. 3 and 4 show two different compounds made by the general method described above. Each compound features fluorescein, a light-emitting moiety, bound to an individual peptide at an amino acid position which preserves the compound's biological activity. In each of these compounds, the C—X bond is an acyl moiety. Table 1, below, lists the peptides and fluorescein-bound amino acids included in each of the compounds.

TABLE 1

Biologically Active Light-Emitting Compounds

| FIG. | Peptide | Binding Amino Acid | Light-emitting moiety |
|---|---|---|---|
| 3 | Endothelin I | 9; ε amine - Lys | fluorescein |
| 4 | Galanin | 5; ε amine - Lys | fluorescein |

The syntheses of the compounds of Table 1, along with biological experiments describing their applications, are described in detail in the Examples below.

In general, any peptide which exhibits an affinity for its corresponding receptor can be used to make a biologically active light-emitting compound of the invention. Peptides may be synthesized using techniques known in the art, extracted from natural systems, or obtained from commercial sources (e.g., Peninsula, Neosystems, Sigma, and BASF). Typically, the peptide is either purchased or synthesized using conventional solid-phase synthetic techniques. Preferably, the peptide is substantially pure, meaning that it is at least 60% by weight free from the other compounds with which it is naturally associated.

In certain peptides, the carboxy terminus is the only part of the molecule which can be attached to a fluorophore without disrupting the peptide's biological activity. In these cases, it is therefore necessary to add a separate "linker" group to the peptide. Since the N-hydroxysuccinimide esters (NHS) or isothiocyanate forms of fluorophores do not readily react with carboxylic groups or carboxyl amine groups, these groups must first be modified to a provide a functional site (e.g., a primary amino group) for conjugation with fluorophores. For example, fluorescent opioid peptides include linker groups to maintain their biological activity. In this case, an aminopentyl group is grafted onto the C-terminal amino acid by aminolysis of the opioid peptide with 1,5-diaminopentane as described below. Aminopentyl linker groups can also be added to a peptide when the peptide is incubated with carbodimides. Water soluble carbodimides are widely used for carboxyl-amine conjugation and may also serve to link fluorophores to the carboxy terminus of peptides.

Whether or not to include a linker group is usually determined empirically by testing a fluorescent peptide labelled at various amino acid sites and finding that it has lost biological activity. For some peptides, structure-activity studies show that the entire amino terminus and central portion of the peptide are involved in receptor binding. This suggests that only the carboxy terminus of the peptide can be modified without disrupting biological activity.

Preferred peptides are included in the group consisting of adrenocorticotrophic hormone, amylin, an amyloid beta-fragment, an atrial natriuretic peptide, bombesin, bradykinin, cadherin, calcitonin, a calcitonin-gene-related peptide, a casomorphin, a morphiceptin, cholecystokinin, corticotropin-releasing factor, deltorphin, a dermorphin, dynorphin, an endorphin, endothelin, enkephalin, fibronectin, galanin, a gonadotropin-associated peptide, a gonadotropin-releasing peptide, a growth factor or growth factor-related peptide, gastrin, glucagon, growth hormone-releasing factor, somatostatin, a GTP-binding protein fragment, inhibin, insulin, interleukin, lutenizing hormone-releasing hormone, magainin, melanocyte-stimulating hormone, a morphiceptin, a neurokinin, a neuromedin, neuropeptide-Y, an opioid peptide, oxytocin, a pancreatic polypeptide, a parathyroid hormone, a vasoactive intestinal polypeptide, Peptide YY, substance P, thyroid-releasing hormone, a toxin, vasopressin, and fragments, derivatives, and analogs thereof.

Peptides useful in the invention include those whose sequences differ from the wild-type peptide sequence by only conservative amino acid substitutions. For example, one amino acid may be substituted for another with similar characteristics (e.g. valine for glycine, arginine for lysine) or by one or more non-conservative amino acid substitutions, deletions, or insertions which do not abolish the peptide's biological activity. Other useful modifications include those which increase peptide stability. For example, the peptide may contain one or more non-peptide bonds (which replace a corresponding peptide bond) or D-amino acids in the peptide sequence.

Other peptides which may be used include those described in the Peninsula Laboratories Inc. catalogue, 1992–1993; SIGMA-Peptides and Amino Acids catalogue, 1993–1994; and PIERCE, Catalog & Handbook, Life Science & Analytical Research Products, 1994, the contents of each of which are incorporated herein by reference.

The light-emitting moiety can be any moiety which emits an optical field following excitation. Preferably, the moiety is selected from the group consisting of fluorescein, FTC, Texas Red, phycoerythrin, rhodamine, carboxytetramethylrhodamine, DAPI, indopyra dyes, Cascade blue coumarin, NBD, Lucifer Yellow, propidium iodide, a porphyrin, BODIPY, $CY^3$, $CY^5$, $CY^9$, and derivatives thereof. Other light-emitting moieties used in labelling or other applications may be attached to the compound in place of the above. For example, suitable light-emitting moieties are described in Molecular Probes, Handbook of Fluorescent Probes and Research Chemicals, 1992–1994; and Richard P. Haugland et al., "Design and Application of Indicator Dyes", Noninvasive Techniques in Cell Biology: 1–20, Wiley-Liss Inc., (1990), the contents of each of which is incorporated herein by reference.

In general, these light-emitting moieties possess at least one side group capable of reacting with amino acids to form chemical bonds. Such side groups include indoacetamide, maleimide, isothyocyanate, succinimidyl ester, sulfonyl halide, aldehyde, glyoxal and hydrazine derivatives. Amino acids including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine may be labelled in this fashion.

In order to retain substantial biological activity and affinity for its receptors, the peptide moiety is attached to the light-emitting moiety by a —(CX)— bond. This bond can include groups such as C=O, C=S, CH(OH), C=C=O, C=NH, $CH_2$, CHOH, CHOR, CNR, CH—R, and C—$R_3R_4$, wherein each R, $R_3$, and $R_4$, independently, is H or a C1–C6 branched or unbranched, substituted or unsubstituted, alkyl.

Fluorescent compounds selected to have high biological activities have a number of uses. For most applications, the compound is first contacted with the sample of interest. The compound is then incubated with the cells or tissues of the sample for a select time period and allowed to interact with the receptor corresponding to the compound's peptide.

Once the peptide is bound to the desired receptor sites, the labelled sample is imaged using standard techniques known in the art. For example, conventional microscopy methods, such as fluorescence or confocal microscopy, may be used to optically excite and then detect emission from the labelled receptors. Other imaging techniques which may be used with the fluorescent peptides include atomic force microscopy, fluorescence polarization spectroscopy, and fluorimetry.

Using the above techniques, small-scale features in the cell which normally would be difficult to detect are observed. For example, these techniques allow visualization of intracellular receptor sites. Moreover, labelled peptides participating in peptide-receptor interactions can be monitored to determine the location of receptors in cells or tissues, to allow quantification of receptors, to determine receptor affinity for various unknown ligands (drug screening), and to identify various populations of cells endowed with peptide receptors. Other applications include receptor sorting using FACS (fluorescence-associated cell sorting) and measurement of serum peptide levels using FIA (fluorescent immunoassays) either in vivo or in vitro for research or diagnostic purposes. In general, techniques which may utilize the compounds of the invention include, without limitation, flow cytometry, cell sorting (for example, to isolate populations of cells bearing a receptor of interest), tumor marking, competitive binding assays for drug screening, fluorescent immunoassays, and other in vitro experimental techniques involving compound labelling according to techniques known in the art.

The following Examples are used to more particularly point out the synthesis, selection methods, and use of fluorescent peptides having substantial biological activity.

EXAMPLES

Example 1

Fluorescent Labelling of Galanin and Endothelin

Twenty five μg of galanin and 20 μg of endothelin purchased from Peninsula Laboratories Inc. (San Carlos, Calif.) were dissolved in separate solutions of 40 μl of 50 mM bicarbonate buffer ($NaHCO_3$), pH 9.3, to a final dilution of 0.8 mM, or 10 μl of the same in the case of endothelin. NHS-fluorescein (N-hydroxy-succinimidyl ester) from Pierce Chemical Company (Rockford, Ill.) was dissolved in 100 μl of DMSO. 50–100 μl of this stock NHS-fluorescein (2.1 μmol) was added while mixing the peptide solution. The sample was then placed on ice, incubated for one hour at pH 9.3, and then brought to pH 8 by the addition of 500 mM Tris HCl. Incubation was allowed to proceed for the next 18 hours at 4° C.

Following incubation, unreacted fluorescein was removed using G-50 column chromatography (Pharmacia Biotech, Upsala, Sweden). Biologically active and inactive compounds were eluted with 0.1 M phosphate buffered saline (PBS) at pH 7.4 by spinning the column in a table-top centrifuge at 3000 rpm for 10 minutes. The eluent was dissolved and incubated with known quantities of rat renal membrane homogenates for endothelin, and rat brain homogenates for galanin. The components of these assays were prepared according to standard techniques, with receptor binding monitored in a Beacon™ fluorescence polarization apparatus from Panvera Corp.

After allowing binding to occur over a 60-minute period for endothelin and galanin, membranes were precipitated from solution by centrifugation at 3000 rpm for 5 minutes at 4° C. Membranes were then resuspended in PBS and incubated with a solution equivalent to 0.5 M NaCl or 0.2 M acetic acid at pH 3.1 to strip surface-bound fluorescent peptides from their receptors on the cell surface. Using this method, the biologically active compounds were then collected for amino acid analysis.

The sites of attachment of fluorescein to endothelin and galanin were confirmed to be at, respectively the ninth amino acid (i.e., lysine) on the epsilon amino group and the fifth amino acid residue (lysine) on the epsilon amino group. The molar ratio of fluorescein to peptide was confirmed to be 1:1 in each case.

Competition binding with radiolabelled endothelin and galanin indicated that the peptides had maintained their biological activity and retained a high affinity for their respective receptors. The $IC_{50}$ for unlabelled galanin, as compared to fluorescent galanin, was 1.75 nM versus 8.86 nM. The $IC_{50}$ is related to the $K_i$ by the formula $IC_{50}=K_i(1+F_L/K_d)$, where $F_L$ is the concentration of the free labelled ligand and $K_d$ is the dissociation constant for the labelled ligand. The $K_i$ for this compound was 1.06 nM versus 5.36 nM. These results indicate a high degree of retention of biological activity.

Example 2

Fluorescent Opioids

As described above, fluorescent opioid peptides can include linker groups to maintain their biological activity. In a particular example, dermorphin, a mu opioid receptor agonist, was originally isolated from the skin of a frog (*Phylomedusa sauvagei*). An analogue of this peptide, [Lys7]dermorphin ($NH_2$-Tyr-Dala-Phe-Gly-Tyr-Pro-Lys-C-$NH_2$), has a very high affinity for the mu opioid receptor, and has a high specificity for the mu receptor when compared to the delta opioid receptors (Negri et al., 1992. Proc. Natl. Acad. Sci. USA 89:7203). Another peptide, deltorphin 1 ($NH_2$-Tyr-Dala-Phe-Asp-Val-Val-Gly-C-$NH_2$), also isolated from the skin of another frog (Phylomedusa bicolor) is an agonist with high affinity and selectivity for delta opioid receptors. Structure-activity studies of opioid peptides suggest that the amino terminus of the peptide is necessary to maintain receptor binding and for conferring overall opioid specificity.

The deltorphin I and [Lys7]dermorphin peptides were modified by adding an linker molecule; this process enabled the coupling of a fluorophore to a previously unreactive or less reactive carboxy terminus amino acid site. The C-terminal amide function (—$CONH_2$) was substituted by an aliphatic chain ending with a primary aminopentyl group (—CONH—$(CH_2)_5$—$NH_2$). The corresponding peptides were then labelled, respectively, on their single amino group with fluorophores.

Preparation of Opioid Precursors

The modified opioid peptides described below were prepared by solid-phase synthesis on a standard Merrifield resin including reticulated polystyrene with 1% divinyl benzene. The aminopentyl group was grafted on the C-terminal amino acid by aminolysis of the peptide resin with 1.5 diaminopentane as described by Goldstein et al., Proc. Natl. Acad. Sci. 85:7375 (1988), the contents of which are incorporated herein by reference. First, the amino acids which are side-chain protected and activated on their carboxylate groups are attached to the resin in a sequential fashion starting from the C-terminus and ending on the N-terminus. The bond between the resin and the peptide is an ester linkage formed from an OH group of the resin and the carboxyl group of the last amino acid.

Using acid hydrolysis, the ester bond between the peptide and resin is then broken in order to introduce the aminopentyl linker group. This process liberates a peptide with a free COOH at the C-terminus. Acid hydrolysis includes incubating the peptide with 10% (v/v) 1.5 diaminopentane in methanol for 60–72 hours at 25° C. This cleaves the ester linkage and replaces it with an amide bond including the C=O moeity of the peptide and one of the amino groups from the 1.5 diaminopentane (either group is acceptable since the molecule is symmetrical).

The amino acid side chains of the peptide are then deprotected by treating the peptide with liquid hydrogen fluoride. Ten milliliters of hydrogen fluoride per gram of peptide was used at 0° C. for 45 minutes in the presence of p-cresol as scavenger. After evaporation of the hydrogen fluoride, the crude reaction mixture is precipitated with diethylether, washed, dried, dissolved in AcOH and lyophilized. The product was then purified by HPLC using a silica $C_{18}$ column (5–25 μm, 100A) 10 nm×250 nm (Althosphere, ODS, Beckman) eluted with 0.1% TFA with a linear gradient of 25% to 70% $CH_2CN/A$ for 30 minutes at a flow rate of 40 ml/min, and optically detected at 210 nm using ultraviolet absorption spectroscopy.

All fractions containing the target compound were individually analyzed by HPLC. Fractions demonstrating sufficient purity were polled and lyophilized. The final products were identified and monitored for purity and identity using analytical HPLC and electron-spin mass spectral analysis. After filtration of the resin, the protected peptide is dissolved in DMF and concentrated with a rotary evaporator. The product is extracted in DCM, with the excess diaminopentane eliminated with $KHSO_4$ (0.01M) washings. After evaporation, the peptide is precipitated with diethylether and dried.

Preparation of Fluorescent Opioids

Opioid precursors described above were reacted with the N-hydroxysuccinimide (NHS) esters of the following fluorophores: Fluorescein, BODIPY 503/512, and BODIPY 576/589 (Molecular Probes, Eugene Oreg.). These three reagents were mixed in different solutions (2 μmoles in 400 μl of dimethyl sulfoxide) and were individually incubated with the deltorphins DLT-1 5APA and [K7] DRM 5APA (2 μmoles) in a final volume of 1 ml of Borate/Phosphate buffer (pH 8.5) for 3 hours at 4° C. The different derivatives were purified by HPLC on a $C_{18}$ column (10 mm×250 mm, Ultrosphere, ODS, Beckman) eluted in TFA (0.1%) with a linear gradient from 20% to 60% over an 80-minute time period. Several fluorescent peaks were identified and tested for their ability to displace the specific binding of iodinated analogues of DLT-1 5APA and [K7]DRM 5APA to the delta and mu opioid receptors, respectively.

The peptides were purified and then subjected to mass spectroscopy for the determination of the molar ratio of the fluorophore-to-peptide labeling. These studies indicated that all peptides were labelled with a single fluorophore. The sequence of each peptide, as well as the position of the fluorophore along the amino acid chain, were determined by Edman's degradation. Peptide sequencing indicated that none of the peptides were labelled on the α-amino group. In addition, no lysine residue could be detected in position 7 for peptide peaks 3 and 5, indicating that these peptides were labelled by a fluorescent group on the lysine side chain. All other peptides were labelled on the amino group of the carboxy-terminus aminopentyl linker.

The biological activity of the peptides was examined by measuring their ability to displace specific binding of iodinated DLT-I 5APA and [K7]DRM 5APA to rat mu and delta opioid receptors expressed by transient transfection in COS cells. Iodinated analogues of DLT-1 5APA and [K7]DRM 5APA (50,000–200,000 cpm) were incubated with delta and mu opioid receptors (5–20 μg) respectively during 30 minutes at 25° C. in 0.25 ml of 0.2% BSA and 50 mM Tris-HCl (pH 7.5). The incubation medium was then diluted in 3 ml of ice-cold incubation buffer and filtered under reduced pressure on GF/C filters presoaked in 0.3% PE1-HCl (pH 7.5). Filters were rinsed by 2×3 ml of ice-cold incubation buffer and counted in a gamma counter. The results of these pharmacological binding experiments are summarized in Table 1.

Fluorescent analogues were also tested for their ability to selectively label mu and delta opioids receptors on COS cells by fluorescent microscopy. Cells in suspension were incubated for 30 minutes in Earle's buffer containing 0.2% BSA and 10 nM BODIPY 513/512 DLT-1 5APA. Cells were spun down, air dried, and then examined by confocal microscopy. Labeling with the fluorescent derivative appeared as punctate labeling of the cell surface membrane and cytoplasm.

TABLE 1

Binding Properties of Fluorescently Labelled Opioid Peptides

| Fluorescent Peptide | Molecular Weight | IC50 (nM) delta | IC50 (nM) mu |
|---|---|---|---|
| DLT-I (Deltorphin) | | 2.3 | 1200 |
| ω-BODIPY 503/512 DLT-I 5APA | 1084 | 2 | 1400 |
| ω-BODIPY 576/589 DLT-I 5APA | 1121 | 2 | 450 |
| ω-FL DLT-I 5APA | 1168 | 26 | >1000 |
| [Lys7]DRM (Dermorphin) | | 0.9 | 740 |
| ω-BODIPY 503/512 [K7]DRM 5APA | 1177 | 10 | 0.6 |
| ω-BODIPY 576/589 [K7]DRM 5APA | 1214 | 21 | 1 |
| ω-BODIPY 503/512 [R7]DRM 5APA | 1205 | 7.2 | 0.6 |
| ω-FL [K7]DRM 5APA | 1261 | 116 | 4.8 |
| ω-FL [R7]DRM 5APA | 1289 | 56 | 3.6 |
| ε-FL [K7]DRM 5APA | 1261 | 436 | 11 |
| ε-BODIPY 503/512 [K7]DRM 5APA | 1177 | 2.6 | 0.7 |
| ε-BODIPY 576/589 [K7]DRM 5APA | 1214 | 14 | 1.8 |

Example 3. Fluorescent peptide labelling of peptide receptors on fresh frozen tissue sections Example 3

Fluorescent Peptide Labelling of Peptide Receptors on Fresh Frozen Tissue Sections Female Sprague Dawley rats were sacrificed by decapitation, and their brains snap-frozen in isopentane at −40° C. Frozen sections of 20 μm from the rat kidney and brain were cut on a cryostat at −20° C. and thaw-mounted on gelatin-coated slides. The sections were dried in a desiccator overnight at −20° C.

Kidney sections were incubated in 500 ml of 10 mM sodium phosphate buffer (pH 7.4) containing 150 mM NaCl, 5 mM $Na_2$-EDTA, and 0.02% $NaN_3$ to remove any endogenous ligand. For fluorescent endothelin labeling, kidney sections were preincubated for 15 minutes in 20 mM HEPES buffer (pH 7.4) containing 135 mM NaCl and 2 mM $CaCl_2$. The sections were then incubated with 2 nM of fluorescent endothelin in 20 mM HEPES buffer (pH 7.4) containing 135 mM NaCl, 2 mM $CaCl_2$, 0.2% BSA, and 0.01% bacitracin for 2 hours at room temperature. For fluorescent galanin labeling, brain sections from the septal region of the forebrain were incubated with 2 nM of fluorescent galanin in 20 mM HEPES buffer (pH 7.4) containing 5 nM $MgCl_2$, 0.1% bacitracine, 1 mM EDTA, 1% BSA for 45 minutes at room temperature.

After incubation, all rat tissue sections were transferred through 4 successive 1-minute washes of PBS buffer (pH 7.4) at 4° C. The slides were then rapidly dried under a cold stream of air and examined using confocal laser scanning microscopy (CLSM) to observe the binding of the fluorescent peptides. Sections were initially examined on a Leica epifluorescence photomicroscope operating with a high-pressure 100 Watt mercury arc lamp; the appropriate dichroic filter combination for the excitation (485 nm) and emission (520 nm) wavelengths of fluorescein was employed to improve the signal-to-noise ratio of the fluorescence signal. Selected portions of the sections were further scanned using a Leica CLSM (St. Laurent, Quebec, Canada) composed of a Leica Diaplan inverted microscope equipped with an argon ion laser (488 nm) having an output power of 2–50 mW. All computer-generated images (i.e., FIGS. 7B–10B) and processing operations were carried out using the Leica CLSM software package.

Referring now to FIGS. 5A, 5B, 6A, and 6B, sections of rat kidney and brain sections incubated with fluorescent endothelin and galanin demonstrated discreet apple-green fluorescent labeling when monitored with the CLSM. Overall, the distribution pattern of fluorescent labeling conformed to that previously determined using radiolabelled analogs of the above peptides. In particular, the experiments indicated that only areas known to contain receptors were labelled while nearby areas devoid of receptors were completely unlabelled. This finding suggests that the compounds of the invention retain the peptides' high specificity for their receptors. In addition, all fluorescent peptide labeling was abolished by incubation with 100-fold excess of unlabelled peptide, further indicating that labeling with the compounds of the invention was selective for the peptides' receptors.

Figure 5A:
FIGS. 5A and 5B are, respectively, CLSM and computer-generated images showing fresh, frozen rat cerebellum sections imaged with fluorescent endothelin; and, FIGS. 6A and 6B are, respectively, CLSM and computer-generated images showing fresh, frozen rat brain septal regions imaged with fluorescent galanin.
Figure 5B:
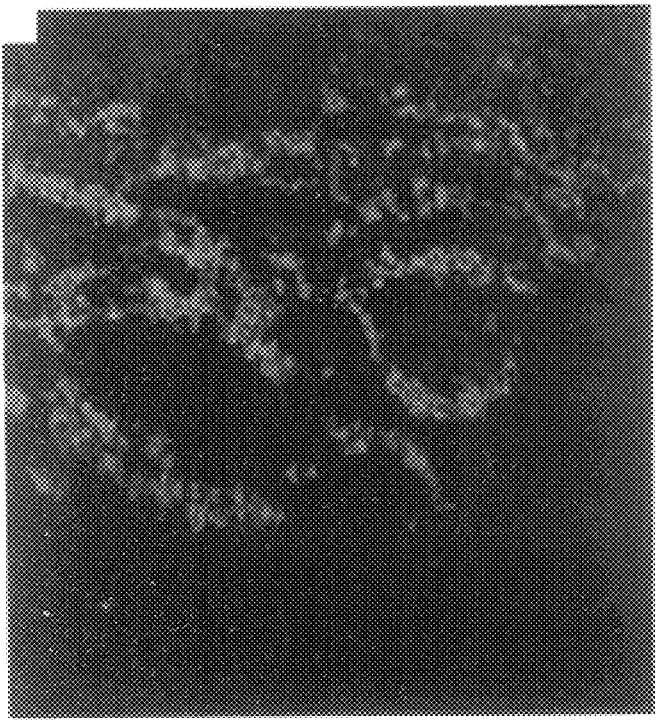

FIGS. 5A and 5B are, respectively, CLSM and computer generated images of fluorescent endothelin binding to 20 μm-thick sections from the rat cerebellum, a region known to be enriched in endothelin receptors. Within the cerebellum, the labeling was confined to a Purkinje cell layer which, at higher power, appeared concentrated throughout Purkinje cell bodies and large dendrites. The adjacent molecular layer, represented in the bottom portion of the photograph, was completely devoid of labeling. Incubation with 100-fold excess unlabelled endothelin resulted in an absence of labeling.

Figure 6A:
Figure 6B:
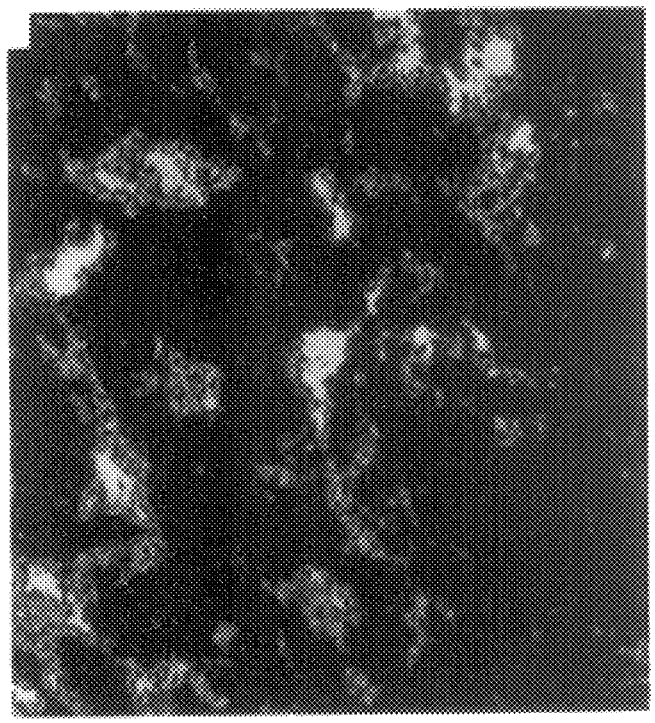

FIGS. 6A and 6B are, respectively, CLSM and computer generated images of fluorescent galanin binding to 20 μm-thick sections from the rat brain septal region at 40X. This region is known to contain galanin receptors. Within the septal area, the labeling was confined to numerous small fusiform neurons and proximal small dendrites, shown in the center and left-hand portions of the images. In the images, the cellular pattern of labeling was diffuse, whereas the dendritic labeling was of higher resolution.

Other embodiments are within the scope of the following claims.

What is claimed is:

1. A biologically active and fluorescent compound of the formula:

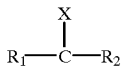

wherein
R$_1$ is a light-emitting moiety;
R$_2$ is galanin, a galanin analog based on conservative amino acid substitutions, a galanin derivative, or a fragment thereof; and
wherein X is selected from the group consisting of =O, =S, —OH, =C=O, =NH, —H, —OR, —NH, —R and R$_3$R$_4$, where each R, R$_3$ and R$_4$ independently is H or a branched or unbranched, substituted or unsubstituted C1–C6 alkyl group.

2. A method for generating a biologically active compound of claim 1, comprising:
reacting R$_1$ and R$_2$ in an aqueous solution to form a compound mixture;
contacting said compound mixture with a receptor for R$_2$; and
isolating from said compound mixture a compound exhibiting biological activity in the presence of said R$_2$ receptor.

3. The method of claim 2, wherein said isolating step comprises
binding said compound to said R$_2$ receptor to form a binding complex;
releasing said compound from said binding complex; and
isolating said biologically active compound.

4. A method for generating a biologically active peptide compound of claim 1, comprising:
reacting R$_1$ and R$_2$ in an aqueous solution to form a compound mixture;
contacting said compound mixture with a receptor for R$_2$;
isolating from the compound mixture a compound exhibiting biological activity in the presence of said R$_2$ receptor;
determining the amino acid position at which said R$_1$ moiety is bound to said R$_2$ peptide; and
synthesizing said compound of claim 1 by chemically attaching said R$_1$ moiety to said amino acid of said R$_2$ peptide.

5. A method for imaging cell receptor sites comprising contacting candidate cell receptor sites with a compound of claim 1, and detecting said bound compounds as an indication of said cell receptor sites.

6. A method for cell sorting comprising contacting a population of candidate cells with a compound of claim 1, and isolating cells bound to said compound.

7. A method for flow cytometry comprising contacting a population of cells with a compound of claim 1 and detecting cells bearing receptors on their surfaces by detecting cells bound to said compound.

8. A compound of claim 1;
wherein said compound is formed by:
reacting R$_1$ and R$_2$ in an aqueous solution to form a compound mixture;
contacting the compound mixture with a receptor for R$_2$;
isolating from the compound mixture a compound exhibiting biological activity in the presence of the R$_2$ receptor;
determining biologically inactive regions of the isolated compound; and
synthesizing said compound by covalently attaching R$_1$ to an amino acid in said biologically inactive region to form a labeled amino acid, and by attaching other amino acids to said labeled amino acid to form said compound.

9. A compound of claim 1, wherein R$_2$ is galanin or a fragment thereof.

10. A compound of claim 1, wherein R$_2$ is a galanin analog based on conservative amino acid substitutions, or a fragment thereof.

11. A compound of claim 1, wherein C(X) is linked to R$_2$ through an alpha carbon atom of an amino acid residue.

12. A compound of claim 1, wherein C(X) is linked to a residue of R$_2$ which is not required for biological activity.

13. A compound of claim 1, wherein R$_2$ binds to a human receptor.

14. A compound of claim 1, wherein C(X) is linked to Lys, the fifth amino acid residue of galanin.

15. A compound of claim 14, wherein C(X) is linked to the epsilon-amino group of a Lys residue.

16. A compound of claim 1, wherein R$_1$ is selected from fluorescein, FTC, Texas Red, phycoerythrin, rhodamine, carboxytetramethylrhodamine, DAPI, indopyra dyes, Cascade blue coumarin, NBD, Lucifer Yellow, propidium iodide, a porphyrin, BODIPY, CY$^3$, CY$^5$, CY$^9$, and derivatives and analogs thereof.

17. A compound of claim 1 wherein C(X) comprises a linking moiety selected from C=O and —C=S.

18. A biologically active and fluorescent compound of the formula:

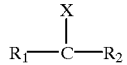

wherein
R$_1$ is a light-emitting moiety;
R$_2$ is neuropeptide Y(NPY), peptide YY(PYY) or a derivative or analog based on conservative amino acid substitutions thereof, or a fragment thereof; and
wherein X is selected from the group consisting of =O, =S, —OH, =C=O, =NH, —H, —OR, —NH, —R and R$_3$R$_4$, where each R, R$_3$ and R$_4$ independently is H or a branched or unbranched, substituted or unsubstituted C1–C6 alkyl group.

19. A compound of claim 18, wherein C(X) is linked to R$_2$ through a lysine residue.

20. A biologically active and fluorescent compound of the formula:

wherein R$_1$ is a light-emitting moiety;
R$_2$ is enkephalin, an enkephalin derivative, or an enkephalin analog based on conservative substitutions, or a fragment thereof, wherein R$_2$ has no more than five amino acid residues; and
C(Z) is (C=O), (C=S), (C=NH), (CH$_2$), or CH(OR), where R is H or a C$_{1-6}$ branched or unbranched, substituted or unsubstituted, alkyl.

21. A compound of claim 20, wherein R$_2$ is enkephalin or a fragment thereof.

22. A method for generating a biologically active compound of claim 21 comprising:

reacting $R_1$ and $R_2$ in an aqueous solution to form a compound mixture;

contacting said compound mixture with a receptor for $R_2$; and isolating from said compound mixture a compound exhibiting biological activity in the presence of said $R_2$ receptor.

23. The method of claim 22, wherein said isolating step comprises binding said compound to said $R_2$ receptor to form a binding complex; releasing said compound from said binding complex and isolating said biologically active compound.

24. A compound of claim 20, wherein $R_2$ is an enkephalin analog based on conservative amino acid substitutions, or a fragment thereof.

25. A compound of claim 20, wherein C(Z) is linked to $R_2$ through an alpha carbon of an amino acid residue.

26. A compound of claim 20, wherein C(Z) is linked to a residue of $R_2$ which is not required for biological activity.

27. A compound of claim 20, wherein $R_1$ is selected from fluorescein, FTC, Texas Red, phycoerythrin, rhodamine, carboxytetramethylrhodamine, DAPI, indopyra dyes, Cascade blue coumarin, NBD, Lucifer Yellow, propidium iodide, a porphyrin, BODIPY, $CY^3$, $CY^5$, $CY^9$, and derivatives and analogs thereof.

28. A compound of claim 20, wherein $R_2$ binds to a human receptor.

29. A method for generating a biologically active peptide compound of claim 20 comprising:

reacting $R_1$ and $R_2$ in an aqueous solution to form a compound mixture;

contacting said compound mixture with a receptor for $R_2$;

isolating from the compound mixture a compound exhibiting biological activity in the presence of said $R_2$ receptor;

determining the amino acid position at which said $R_1$ moiety is bound to said $R_2$ peptide; and synthesizing said compound of claim 20 by chemically attaching said $R_1$ moiety to said amino acid of said $R_2$ peptide.

30. A method for imaging cell receptor sites comprising contacting candidate cell receptor sites with a compound of claim 20, and detecting receptor bound compounds as an indication of said cell receptor sites.

31. A method for cell sorting comprising contacting a population of candidate cells with a compound of claim 20, and isolating cells bound to said compound.

32. A method for flow cytometry comprising contacting a population of cells with a compound of claim 20 and detecting cells bearing receptors on their surfaces by detecting cells bound to said compound.

33. A compound of claim 20 wherein said compound is formed by:

reacting $R_1$ and $R_2$ in an aqueous solution to form a compound mixture;

contacting the compound mixture with a receptor for $R_2$;

isolating from the compound mixture a compound exhibiting biological activity in the presence of the $R_2$ receptor;

determining biologically inactive regions of the isolated compound; and synthesizing said compound by covalently attaching $R_1$ to an amino acid in said biologically inactive region to form a labeled amino acid, and by attaching other amino acids to said labeled amino acid to form said compound.

34. A biologically active and fluorescent compound of the formula:

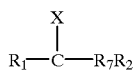

wherein $R_1$ is a light-emitting moiety;

$R_2$ is an opioid peptide that binds to a mu or delta opioid receptor which is not neurotensin;

$R_7$ is a C1–C6 branched or unbranched, substituted or unsubstituted, alkyl; and X is selected from the group consisting of =O, =S, —OH, =C=O, —NH, —H, —OR, —NR, —R, and $R_3R_4$, wherein each R, $R_3$, and $R_4$, independently, is H or a C1–C6 branched or unbranched, substituted or unsubstituted, alkyl.

35. The compound of claim 34, wherein $R_7$ is —NH—$(CH_2)_5$—NH—.

* * * * *

UNITED STATES PATENT AND TRADEMARK OFFICE
CERTIFICATE OF CORRECTION

PATENT NO. : 6,054,557
DATED : April 25, 2000
INVENTOR(S) : Marie-Pierre Faure, Jean-Pierre Vincent, Georges Gaudriault, Alain Beaudet, Clarissa Desjardins It is certified that error appears in the above-identified patent and that said Letters Patent is hereby corrected as shown below:

Title page,
Under "Other Publications":

Sixth reference, first line, please delete "1173" and insert -- 173 --

Page Two,
Under "Other Publications":

Twelfth reference, first line, please delete "Neuropanatomy" and insert
-- Neuroanatomy --

Column 12,
Line 59, (directly below table 1) please delete the first instance of "Example 3. Fluorescent peptide labelling of peptide receptors on fresh frozen tissue sections"

Column 13,
Line 17, please delete "nM" and insert -- mM --

Column 16,
Line 30, please delete "C=O" and replace with -- -C=O --

Signed and Sealed this

Fourteenth Day of August, 2001

*Attest:*

*Attesting Officer*

NICHOLAS P. GODICI
*Acting Director of the United States Patent and Trademark Office*